(12) United States Patent
Mantovani

(10) Patent No.: US 9,808,239 B2
(45) Date of Patent: Nov. 7, 2017

(54) DEVICE FOR THE TRANSOSSEOUS INSERTION OF SUTURE THREADS

(75) Inventor: Matteo Mantovani, Reggio Emilia (IT)

(73) Assignee: NCS LAB S.R.L., Carpi (IT)

(*) Notice: Subject to any disclaimer, the term of this patent is extended or adjusted under 35 U.S.C. 154(b) by 0 days.

(21) Appl. No.: 14/233,255

(22) PCT Filed: Jun. 29, 2012

(86) PCT No.: PCT/IB2012/053319
§ 371 (c)(1),
(2), (4) Date: Jan. 16, 2014

(87) PCT Pub. No.: WO2013/014553
PCT Pub. Date: Jan. 31, 2013

(65) Prior Publication Data
US 2014/0135802 A1    May 15, 2014

(30) Foreign Application Priority Data

Jul. 22, 2011 (IT) .............................. MO2011A0178

(51) Int. Cl.
*A61B 17/04* (2006.01)
*A61B 17/06* (2006.01)
*A61B 17/00* (2006.01)

(52) U.S. Cl.
CPC ...... *A61B 17/0482* (2013.01); *A61B 17/0483* (2013.01); *A61B 17/06066* (2013.01);
(Continued)

(58) Field of Classification Search
CPC ............ A61B 27/0482; A61B 17/0483; A61B 17/06066; A61B 2017/00867;
(Continued)

(56) References Cited

U.S. PATENT DOCUMENTS

| 4,459,978 A | 7/1984 | Kotsanis |
| 5,199,419 A | 4/1993 | Remiszewski et al. |

(Continued)

FOREIGN PATENT DOCUMENTS

| DE | 9106506 U1 | 7/1991 |
| EP | 0380874 A1 | 8/1990 |

(Continued)

OTHER PUBLICATIONS

Machine Translation of JP 2009-268632 : Hayashi, Aid for Artificial Tendon Reconstruction, JP 2009268632A, Nov. 19, 2009.*

*Primary Examiner* — Katherine M Shi
*Assistant Examiner* — Mohamed Gabr
(74) *Attorney, Agent, or Firm* — Pearne & Gordon LLP

(57) ABSTRACT

A device for the transosseous insertion of suture threads comprises: —a main body (1), equipped with a grip (2), supporting a protruding cannula (3) provided with an active end (30); —a flexible thread-like element (4) which is housed in a coaxially sliding manner inside the cannula (3) and is suitable, on command, for exiting from the active end (30) of the cannula (3). The thread-like element (4) is made of a super-elastic, shape-memory material and thus has the property of freely assuming, at least in an adequate temperature range for which its operative use is foreseen, a natural and predetermined curved form at least in a determined portion of the terminal part thereof. Means are provided for producing the coaxial movement of the thread-like element (4) in the two directions relative to the cannula (3).

12 Claims, 3 Drawing Sheets

(52) U.S. Cl.
CPC ........... *A61B 2017/00867* (2013.01); *A61B 2017/0608* (2013.01); *A61B 2017/06019* (2013.01); *A61B 2017/06042* (2013.01)

(58) Field of Classification Search
CPC ......... A61B 2017/06019; A61B 2017/06042; A61B 2017/06088; A61B 17/0482; A61B 17/0469
USPC .................................................. 606/144, 148
See application file for complete search history.

(56) References Cited

U.S. PATENT DOCUMENTS

| | | |
|---|---|---|
| 5,381,788 A | 1/1995 | Matula et al. |
| 5,382,228 A * | 1/1995 | Nita ............... A61B 17/22012 601/3 |
| 5,486,183 A | 1/1996 | Middleman et al. |
| 5,554,101 A | 9/1996 | Matula et al. |
| 5,573,542 A | 11/1996 | Stevens |
| 5,720,754 A | 2/1998 | Middleman et al. |
| 5,722,980 A * | 3/1998 | Schulz ............ A61B 17/22012 604/22 |
| 5,741,278 A * | 4/1998 | Stevens .................... 606/144 |
| 2005/0261718 A1 | 11/2005 | Petros et al. |
| 2006/0258897 A1 | 11/2006 | Petros et al. |
| 2009/0216250 A1 | 8/2009 | Zipper |
| 2010/0298832 A1 | 11/2010 | Lau et al. |
| 2010/0324506 A1 | 12/2010 | Pellegrino et al. |
| 2011/0106124 A1 | 5/2011 | Beauchamp |

FOREIGN PATENT DOCUMENTS

| | | |
|---|---|---|
| EP | 0531710 A1 | 3/1993 |
| FR | 325846 A | 5/1903 |
| JP | 003256540 B2 | 2/2002 |
| SU | 736949 A1 | 5/1980 |
| WO | 2009/133715 A1 | 11/2009 |

\* cited by examiner

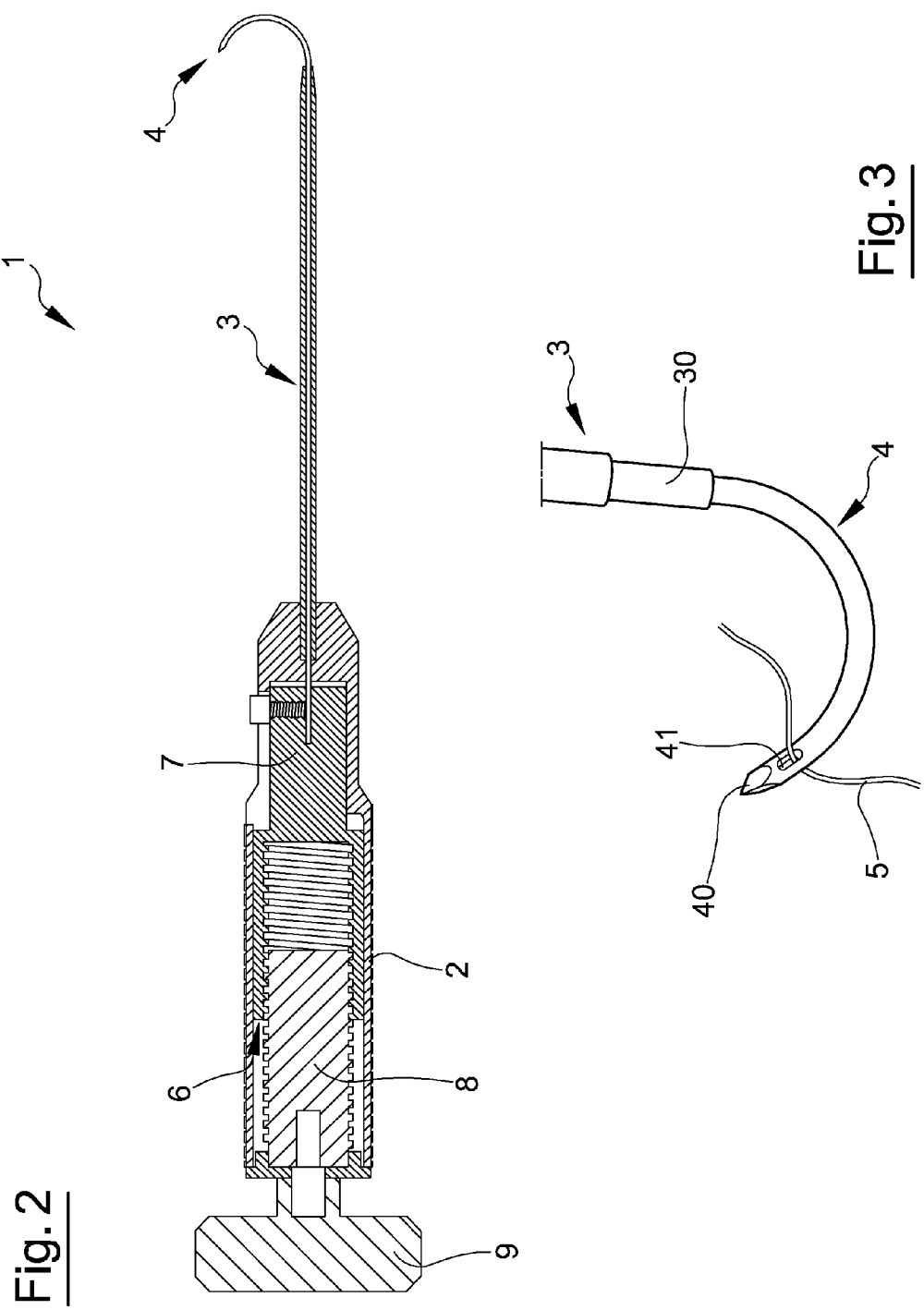

DEVICE FOR THE TRANSOSSEOUS INSERTION OF SUTURE THREADS

The present invention relates to a device for the transosseous insertion of suture threads.

Specifically, but not exclusively, it represents an instrument conceived to help the surgeon to carry out the positioning of suture threads through bones. In particular, it reveals its usefulness in many operations requiring transosseous suture threads to be disposed along non-rectilinear "paths". Typical examples of these types of operations are the ones performed to repair lesions of the rotator cuff tendon.

In the specific case of disposing transosseous suture threads along non-rectilinear "paths", the prior art envisages operations that are relatively complex, also with the use of special instruments, and characterized in any case by a not inconsiderable duration; they essentially consist of two steps: a first step of preparing the hole, which is achieved by making several rectilinear holes that meet so as to design a "path" in the form of a piecewise linear curve for the suture thread, and a second subsequent step which simply consists in introducing the suture thread.

In fact, the holes composed of two rectilinear portions that delineate in any case a "path" in the form of a piecewise linear curve can cause problems of "impingement" with the suture thread.

It should also be noted that the prior art, besides entailing a certain laboriousness, can easily lead the surgeon astray.

The objects of the present invention are to facilitate the execution of the operation and to reduce, accordingly, the times thereof compared to the prior art.

Among the various advantages of the invention, one may mention its simplicity, both structural and operative, and ease of use.

Further features and advantages of the invention will be more apparent from the detailed description that follows of preferred, but not exclusive, embodiments of the invention, illustrated by way of non-restrictive example in the appended figures, in which:

FIG. 2 shows a schematic longitudinal section of the embodiment shown in FIG. 1;

FIG. 3 shows a detail of FIG. 2 on an enlarged scale;

Figure 1:
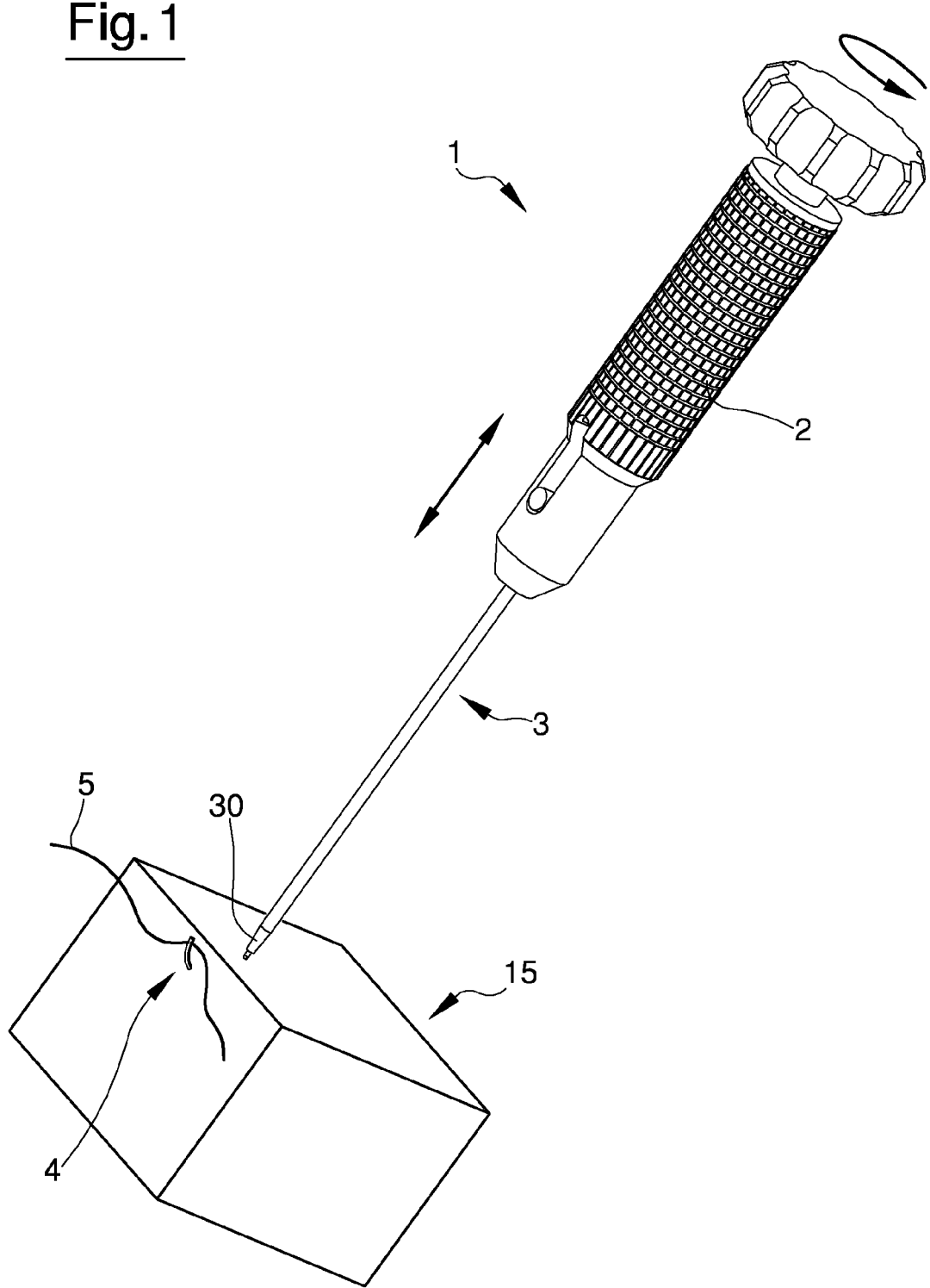
FIG. 1 shows a schematic overall perspective view in which a first embodiment is illustrated through an application to a synthetic bone.

With reference to the appended figures, 1 indicates the main body of a device for the transosseous insertion of suture threads 5.

The main body 1 is equipped with a grip 2 and bears, integrally supported, a cannula 3, which is protruding and provided with an active end 30 specifically configured to enable resting upon the bone surface.

A flexible thread-like element 4 is housed in a coaxially sliding manner inside the cannula 3 and is suitable, on command, for exiting from the active end 30 of the cannula 3.

The thread-like element 4 has the property of freely assuming, that is, when not sheathed in the cannula 3 and at least in an adequate temperature range for which its operative use is foreseen—this temperature range comprising within it room temperature—a natural and predetermined curved form at least in a determined portion of the terminal part thereof.

Specific means, which will be illustrated below, have the task of producing the coaxial movement of the thread-like element 4 in the two directions relative to the cannula 3, thereby causing it both to exit from and re-enter the active end 30.

The thread-like element 4 has particular properties and is made of a super-elastic, shape-memory material.

Moreover, the thread-like element 4 is provided, at the free end thereof, with a sharp tip 40, whose task is to realize and facilitate the perforation of bone tissue, schematically represented by a block 15, and which has, at the free end thereof, a small eye-like opening or eyelet 41 suitable for threading at least one suture thread 5.

In this case the small opening or eyelet 41 is obtained in the sharp tip 40.

The thread-like element 4 is preferably made of an alloy of Nickel and Titanium, where the two elements are present in very similar atomic percentages.

The characteristics of the alloy impart superelasticity and shape memory so that the said pre-established curved form manifests itself at least in a determined portion of the terminal part of the thread-like element 4 once the latter is no longer contained inside the cannula 3.

In this situation and within the envisaged range, which includes room temperature, the curved form is preferably and characteristically hook-shaped, as shown, for example, in FIG. 3.

The means for producing the coaxial movement of the thread-like element 4 in the in the two directions relative to the cannula 3 comprise, in a first embodiment, a screw device 6 by means of which the translation of an element 7 whereto the thread-like element 4 is fastened can be achieved in both directions.

The element 7 is slidably coupled inside the main body 1 externally equipped with the grip 2, and is provided with an internal thread whereby it is coupled with an operating screw 8 that can be activated by means of an external knob 9.

To facilitate the manoeuvre of insertion and perforation of the thread-like element in the bone tissue (schematically represented by the block of material 15), the screw device 6 is preferably realized with a multiple start screw.

The preferred functioning of the device involves carrying out the following steps:

inserting the suture thread 5 through the small opening or eyelet 41;

retracting the thread-like element 4 all the way, i.e. to the active end 30 of the cannula 3;

resting the sharp tip 40 on the bone surface to be perforated;

pushing the thread-like element 4, making it exit from the cannula 3, which remains resting upon the bone surface and pressed against it; in this step the thread-like element 4, on freeing itself from the containment of the cannula 3, reacquires the curved configuration, by virtue of shape memory, enabling the sharp tip 40 to realize, during penetration, a curved path that passes through the bone until the sharp tip itself exits therefrom;

taking the suture thread 5 held by the small opening 41 during the preceding operation in order then to proceed with further use;

withdrawing the thread-like element 4 until extracting it completely from the curved channel obtained, in which the suture thread 5 remains inserted.

The use of the device enables a complete perforation to be achieved and thus in addition to the perforation of a single cortical wall enables a double perforation to be achieved, i.e. perforation of the cortex at the bone entrance and exit.

A variant of the method illustrated can envisage that the insertion of the thread-like element 4 occurs without first inserting the suture thread 5, which is instead inserted once the curved channel or "path" is completed and inserted into it only at the end, i.e. in the step of withdrawing the curved element 4 until the complete extraction thereof from the bone.

Figure 4:
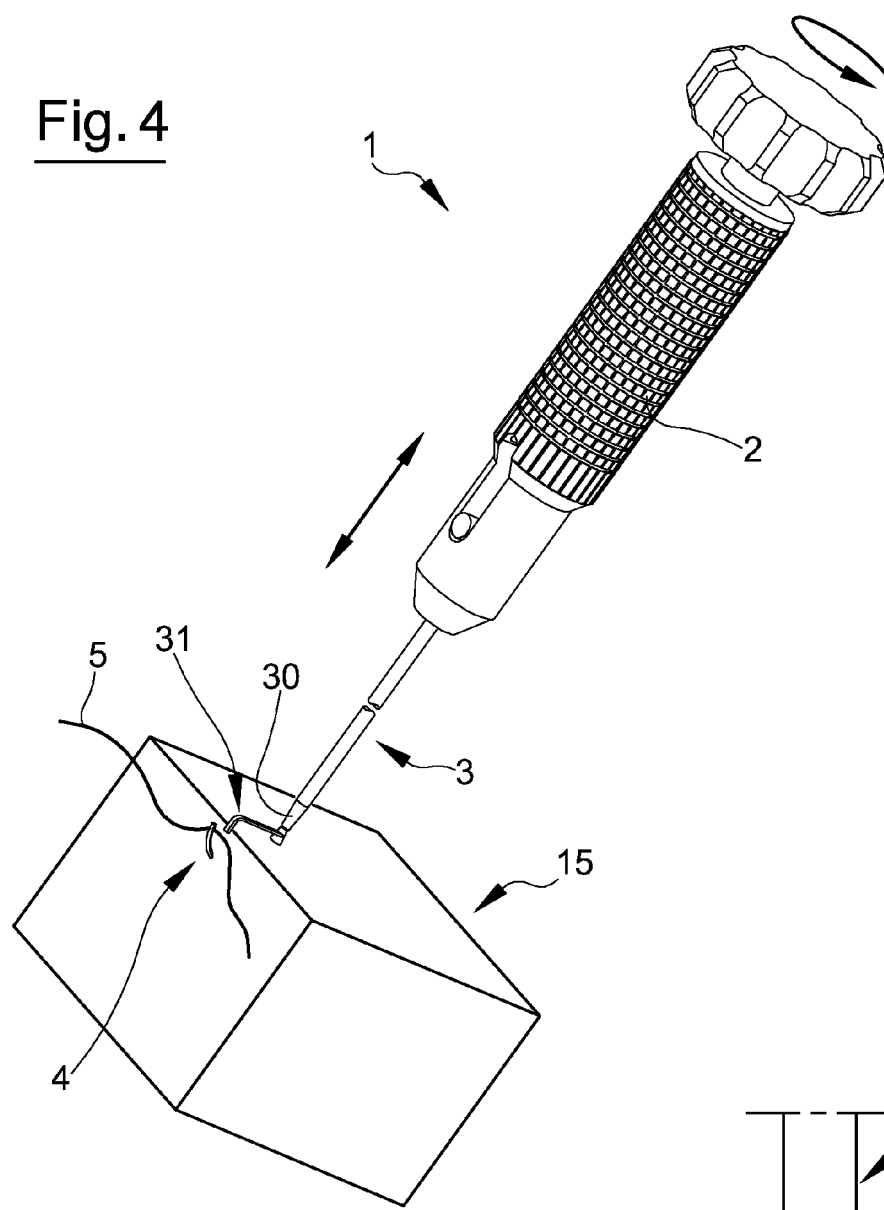
FIG. 4, shows a schematic overall perspective view concerning a second embodiment of FIG. 4 in which an application to a bone is represented.
Figure 5:
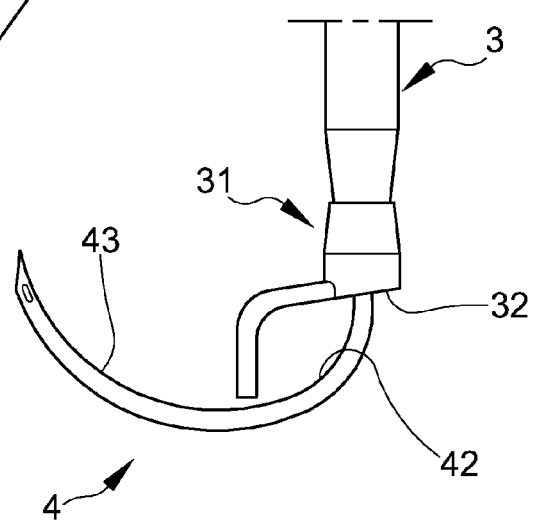
FIG. 5 shows a side view of a detail of FIG. 4 on an enlarged scale.

In a second embodiment, illustrated in FIG. 4, the protruding cannula 3 is provided with an active end 30, constrained to which there is an indicator device 31 disposed coplanar with the plane in which the said curved, hook-shaped terminal part of the thread-like element 4 lies once it has exited from the end of the cannula 3. The indicator device 31 enables the surgeon to foresee, based on the positioning of the device on the bone, the exit point of the sharp tip and hence the exit end of the curved transosseous channel.

The indicator device 31 is interchangeable and has different heights. This makes it possible to operate with different sizes. Two different dimensions are usually sufficient.

In particular, the device is created to have an entrance hole in an area preferably ranging from 10 mm to 30 mm from the tip of the greater tubercle of the humerus. This makes it possible to obtain almost identical exit position, the entrance inclination being equal.

This result is assured by the double curvature of the thread-like element 4 made of super-elastic material, whose pre-established curved, hook-shaped form has at least two portions with a different curvature 42, 43 disposed consecutively to each other and by means of which different perforations can be made, each using an indicator device 31 thereof.

Each indicator device is also provided with a suitable resting base 32, by means of which the whole tool can be conveniently rested upon the surface to be perforated without producing a cortical breakthrough or an unwanted "slotting" of the hole, consisting in a hole characterized in that it is bigger than the diameter necessary to enable the snug insertion of the thread-like element 4 and/or has an irregular contour.

The presence of the indicator device 31 renders the perforation manoeuvre extremely rapid and precise. The device just described can be used to implement a method for the transosseous insertion of suture threads 5, which essentially comprises the insertion by force of a flexible thread-like element 4 from the outside, starting from an entrance area in the cortical zone of a bone, such as to cause it to pass through completely, through the cortical parts and the spongy zone as well, therefore, and exit from an opposite cortical zone following a curved path.

The operation, which comprises making a curved "path", channel or through hole is carried out using said thread-like element 4, which is made of a super-elastic shape-memory material and is provided, at the free end thereof, with a sharp tip 40, which enables penetration and small eye-like opening 41 whose function is to enable the threading of a suture thread 5, which, depending on the operating mode, can be first threaded through the small opening 41 and directly accompany the insertion step.

The forced insertion is achieved by approaching the cortical entrance zone with the end of a cannula 3 housing within it, in an axially sliding manner, the thread-like element 4, which has the property of freely assuming, at least in an adequate temperature range for which its operative use is foreseen, a predetermined curved form at least in a determined portion of the terminal part thereof. The precise predetermination of the position of the exit hole is made possible by the use of the indicator device 31.

Once the perforation of the bone is terminated with the exit of the sharp tip 40 therefrom, the suture thread 5 held by the small opening 41 and inserted into the hole produced can be grasped in order then to proceed with a further operating step.

According to another operating mode, the suture thread 5 is not inserted into the small opening 41 at the beginning of the forced insertion of the thread-like element 40, but rather on completion of the said operation and is inserted into the transosseous hole just fashioned by virtue of the withdrawal of the thread-like element 4 until the exit thereof from the initial cortical entrance zone.

The invention claimed is:

1. A device for the transosseous insertion of suture threads characterized in that it comprises:
    a. a main body (1), equipped with a grip (2), supporting a protruding cannula (3) provided with an active end (30);
    b. a flexible thread-like element (4) housed in a coaxially sliding manner inside the said cannula (3) suitable, on command, for exiting from the active end (30) of the cannula (3), and having the property of freely assuming, at least in an adequate temperature range for which its operative use is foreseen, a natural and predetermined curved form at least in a determined portion of the terminal part thereof; and
    c. means for producing the coaxial movement of the thread-like element (4) in the two directions relative to the cannula (3), said means comprising a screw device which can be axially translated in both directions; the thread-like element (4) being directly fastened to the screw device; said screw device being slidably coupled inside the main body (1) and being provided with an internal thread, said internal thread being coupled with an external thread of an operating screw (8), wherein the operating screw (8) can be activated by means of an external knob (9) so that when the external knob (9) is rotated, the operating screw (8) also rotates, and when the operating screw (8) rotates, the screw device slides (a) axially inside the main body (1), (b) axially relative to the operating screw (8) and (c) axially relative to the main body (1); and wherein the external knob (9) does not axially move relative to the grip (2) when the external knob (9) is rotated.

2. The device according to claim 1, characterized in that the said thread-like element (4) is made of a super-elastic material.

3. The device according to claim 2, characterized in that the said thread-like element (4) is made of a shape-memory material.

4. The device according to claim 1, characterized in that the said thread-like element (4) is made of a shape-memory material.

5. The device according to claim 4, characterized in that the said thread-like element (4) is made of an alloy of nickel and titanium, where the two elements are present in very similar atomic percentages.

6. The device according to claim 1, characterized in that the said thread-like element (4) is provided with a sharp tip (40) at a free end thereof.

7. The device according to claim 1, characterized in that the said thread-like element (4) is provided, at a free end thereof, with a small eye-like opening (41) suitable for threading at least one suture thread (5).

8. The device according to claim 7, characterized in that the said small eye-like opening (41) is obtained in a sharp tip (40) at the free end of the thread-like element (4).

9. The device according to claim 1, characterized in that the said predetermined curved form predisposed at least in a determined portion of the terminal part of the said thread-like element (4) is hook-shaped.

10. The device according to claim 9, characterized in that the said predetermined hook-shaped form of the said thread-like element (4) has at least two portions with a different curvature (42), (43) disposed consecutively to each other.

11. The device according to claim 1, characterized in that an indicator device (31) is (a) constrained to the active end (30) and (b) is disposed coplanar with a plane in which the determined portion of the terminal part of the thread-like element (4) lies.

12. The device according to claim 11, characterized in that the indicator device (31) is interchangeable and has different heights.

* * * * *